Figures 1, 2:
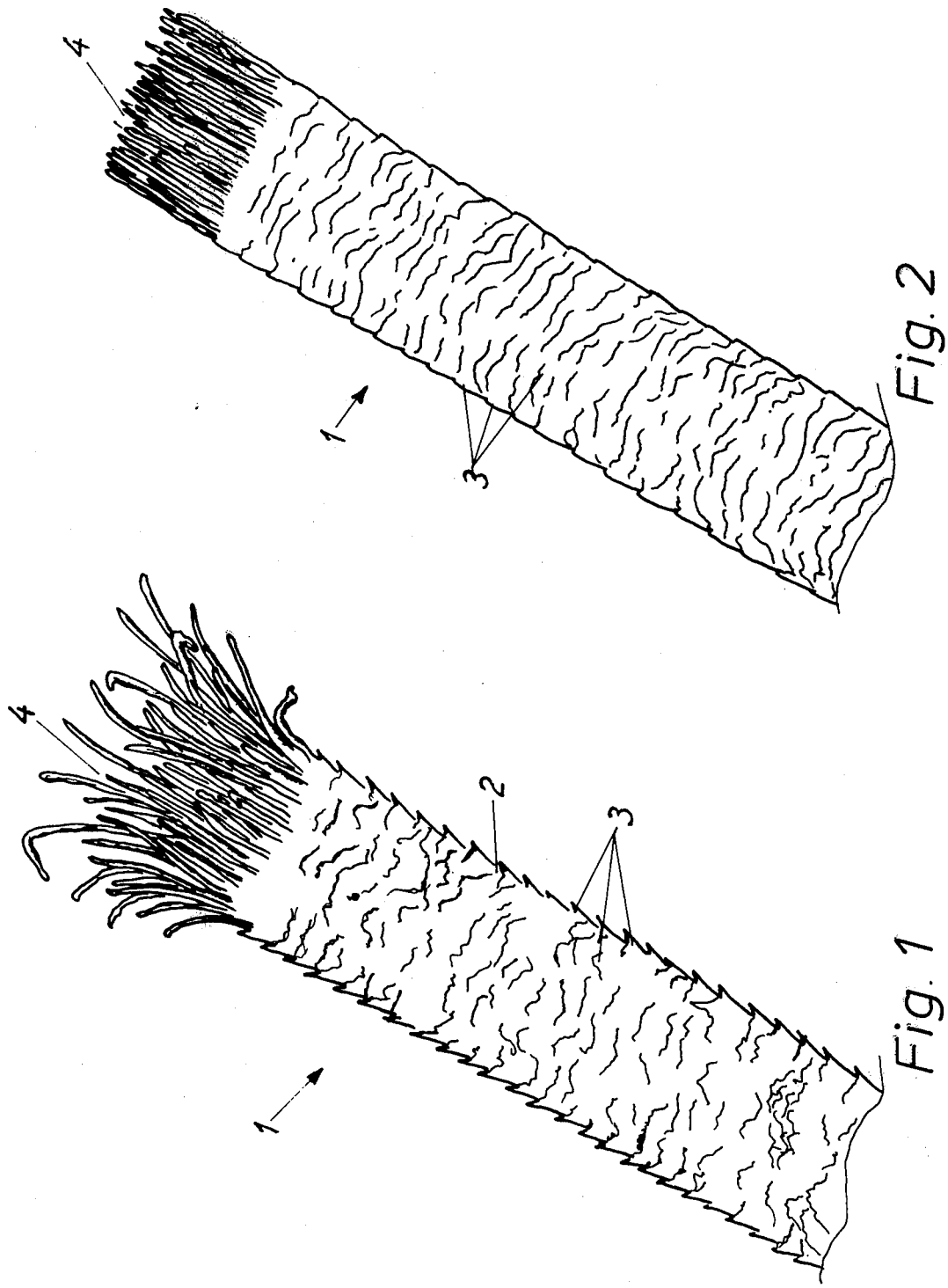

United States Patent [19]

Borchorst

[11] 4,070,452

[45] Jan. 24, 1978

[54] METHOD OF TREATING HAIR WITH A SHAMPOO CONTAINING HONEY

[76] Inventor: Birgit Borchorst, 39 Kystvej, 3100, Hornbaek, Denmark

[21] Appl. No.: 669,910

[22] Filed: Mar. 24, 1976

[30] Foreign Application Priority Data

Apr. 3, 1975    United Kingdom ............... 13577/75

[51] Int. Cl.$^2$ ................................................ A61K 7/06
[52] U.S. Cl. ............................ 424/70; 252/DIG. 13; 252/DIG. 14; 252/544; 424/361
[58] Field of Search ................................. 424/70, 361; 252/DIG. 13, DIG. 14, 544

[56] References Cited

U.S. PATENT DOCUMENTS 3,149,042   9/1964   Habicht et al. ....................... 424/70

OTHER PUBLICATIONS

Balsam et al., Cosmetics—Science & Technology, 2nd Ed., vol. 2, Wiley-Interscience, New York, 1972, pp. 97 and 100.

Caswell Massey, Winter Catalogue, Caswell-Massey Co. Ltd., 320 West 13th St., New York, N.Y. (1972), pp. 36–37.

*Primary Examiner*—Albert T. Meyers
*Assistant Examiner*—Vera C. Clarke
*Attorney, Agent, or Firm*—Burgess, Ryan and Wayne

[57] ABSTRACT

A shampoo composition containing a conventional detergent and honey is disclosed. Optional ingredients are a foam stabilizer, a viscosity adjusting agent, perfume, and a preservative.

4 Claims, 2 Drawing Figures

METHOD OF TREATING HAIR WITH A SHAMPOO CONTAINING HONEY

SUMMARY OF THE INVENTION AND DESCRIPTION OF THE PREFERRED EMBODIMENT

The invention relates to a shampoo for the washing of hair such as human hair. This shampoo comprises an aqueous solution of a surfactant, mainly a fatty alcohol sulphate and perhaps a foam-amplifier in a quantity of 0.5 to 5 percent by weight based on the weight of the product and if necessary a viscosity-adjusting agent in a quantity of 0.5 to 5 percent by weight based also on the weight of the product.

In order to give the hair abundance and better retention of a laid permanent wave such a shampoo may further contain a water soluble material, such as a resinous material, which is also soluble in the aqueous surfactant-system of which the shampoo consists. This material is hair substantive and when using the shampoo, part of the material is adsorbed to the hair where it remains as a cosmetic preparation on the hair after washing and rinsing.

Previously known shampoo-means of this kind, however, have not met the expectations as too small quantities of the material remains to give sufficient cosmetic influence on the hair. Therefore the hair does not have sufficient abundance, which means that the hair does not look full and thick, and the hair is not easy to control and to maintain in a certain wave.

It is the purpose of the invention to supply these wants of the previously known shampoo-means and his is obtained when the shampoo according to the invention furthermore contains honey which is deposited on the hair by dilution of the shampoo during use and which partly gives the hair abundance and maintains the wave and which partly serves as a lubricating agent for the hair.

In practice it has turned out that this admixture of honey partly gives a previously unknown abundance and ability to receive and maintain a certain wave while the honey itself makes up a lubricating means for the hair which makes it easier to comb. Thus, the usual admixtures of mineral oil or organic oil as a lubricating means is avoided. A proper quantity of honey will be between 3 and 20 percent calculated on the weight of the product and in order to ensure a prolonged storage of the shampoo it will be further appropriate to add a preservative.

In the following, the invention will be described in details with reference to the drawing where FIG. 1 shows a close-up of a hair washed with a prior art composition, and FIG. 2 shows a close-up of the same hiar having been washed with the shampoo according to the invention.

FIG. 1 shows the outermost part of a hair 1 as it appears in an enlargement having been washed with one of the generally known shampoo-means. The outermost coating, the outer-pellicle 2, which is made out by a layer of thin, sheet-shaped, tight-fitting cells, appears as small dandrufflike irregularities 3, evenly distributed over the whole hair 1. The point 4 of the hair is split and forms a frayed end with a tendency to splitting over a greater part of the point 4 of the hair. A hair of this appearance will be apt to hang together with the other hairs and thus be difficult to comb. Additionally the hair seems lustreless and is less pleasant to the touch.

FIG. 2 shows a hair having been washed with the shampoo according to the rest of the hair in such a way that the hair 1 appears more smooth. The point 4 of the hair is no longer frayed but lies with the flaps closely gathered in the elongation of the hair.

From the drawing it will be understood why adding of an extra lubrication agent is not necessary when using the shampoo-means according to the invention as the honey by its adsorption to the hair causes a smoothing out and a binding together of the outermost parts of the hair. This gives the hair abundance as the individual hairs will not be likely to hang together.

The following example illustrates the composition of the shampoo according to the invention.

|  | Percentage by weight |
|---|---|
| Fatty alcohol sulphate | 40.0 |
| Honey | 10.0 |
| Coco-fattyacid-diethanolamid | 3.0 |
| Viscosity-adjusting means (NaCl) | 3.0 |
| Methyl- and propylparaben | 0.1 |
| Perfume | 1.0 |
| Water | 42.9 |
|  | 100.0 |

The shampoo-composition according to the present invention contains one or more surfactants. Salts of sulphonated and sulphonated anionic surfactants are preferred. As an example of suitable anionic detergents laurylether-sulphate can be mentioned. Such a surfactant is available from Henkel & Cie, GmbH, Dusseldorf, West Germany under the registered name "TEXAPON ASV".

The honey is obtained from commerce with an average water content of 20 percentage by weight and a sugar content of 73 percentage by weight. A genuine bee-honey is preferable but it is within the scope of the invention to use a so-called artificial honey.

Further the shampoo may contain between 0.5 and 5 percentage by weight of one or more foam-amplifying and/or -stabilizing means for increasing the foamability and the foam stability. Examples of such connections are coco-fattyacid-diethanolamid which furthermore makes up a waxy-material, that gives the hair additional abundance and has a conditioning effect on it.

Further a viscosity-adjusting agent such as NaCl may be added. The quantity of the salt depends on the desired viscosity of the shampoo.

A preservative may be required and for this purpose methyl- and propyl-paraben are used.

Furthermore, additional additives may be added to the shampoo if desired for instance perfumes, etheric-oil or colorants in order to improve the commercial value of the shampoo.

The rest of the product consist of water.

I claim:

1. A method of treating hair to impart luster thereto and better retention of a wave which comprises shampooing the hair with an effective amount of a composition comprising
   A. an effective amount of an anionic detergent;
   B. 0.5–5 percent by weight of a foam stabilizer;
   C. 0.5–5 percent by weight of a viscosity adjusting agent;
   D. 3–20 percent by weight of honey and
   E. balance water.

2. A method according to claim 1 wherein said composition also includes a preservative.

3. A method according to claim 1 wherein said composition also includes a perfume.

4. A method of treating hair to impart luster thereto and better retention of a wave which comprises shampooing the hair with an effective amount of a composition which comprises, in percent by weight,

| | | |
|---|---|---|
| A) | a fatty alcohol sulfate | 40.0 |
| B) | coco fatty acid diethanolamide | 3.0 |
| C) | sodium chloride | 3.0 |
| D) | honey | 10.0 |
| E) | methyl- and propyl-paraben | 0.1 |
| F) | perfume | 1.0 |
| G) | water | 42.9 |
| | TOTAL | 100.0 |

* * * * *

UNITED STATES PATENT OFFICE
CERTIFICATE OF CORRECTION

Patent No. 4,070,452             Dated March 20, 1978

Inventor(s) Birgit Borchorst

It is certified that error appears in the above-identified patent and that said Letters Patent are hereby corrected as shown below:

Column 1, line 33: "his" should be --this--.

Column 1, line 55: "hiar" should be --hair--.

Column 2, line 2: after "according to the" should be inserted -- invention. It appears how the sheet-shaped cells 3 lie close to the--.

*Signed and Sealed this*

*Twenty-seventh* Day of *June 1978*

[SEAL]

Attest:

RUTH C. MASON
*Attesting Officer*

DONALD W. BANNER
*Commissioner of Patents and Trademarks*